United States Patent [19]

Karjalainen et al.

[11] Patent Number: 4,514,412

[45] Date of Patent: * Apr. 30, 1985

[54] SUBSTITUTED IMIDAZOLE DERIVATIVES AND THEIR USE AS ANTI-THROMBOSIS AGENTS

[75] Inventors: Arto J. Karjalainen; Kauko O. A. Kurkela, both of Oulu, Finland

[73] Assignee: Farmos Yhtyma Oy, Turku, Finland

[*] Notice: The portion of the term of this patent subsequent to Apr. 17, 2001 has been disclaimed.

[21] Appl. No.: 345,548

[22] Filed: Feb. 3, 1982

[30] Foreign Application Priority Data

Feb. 5, 1981 [GB] United Kingdom ............... 8103620

[51] Int. Cl.³ ................. A61K 31/415; C07D 233/54; C07D 233/66
[52] U.S. Cl. .................................. 514/397; 548/342; 548/343; 548/235
[58] Field of Search .................. 548/342, 343, 235; 424/273 R; 542/458, 468, 400

[56] References Cited

PUBLICATIONS

Schubert, et al., CA 60:14495c.
Wegner, et al., CA 85:46504a.
Iwasaki, CA 86:106471z.
J. Am. Chem. Soc., 95:1, 1973, pp. 284–285, Wuonola, et al.
J. Org. Chem., 39, pp. 2301–2302, Noyce, et al.
Chem. Abs., 71:124547u; Soniun, et al.
Chem. Abs., 52:4494i, Lawson.

Primary Examiner—Henry R. Jiles
Assistant Examiner—Robert C. Whittenbaugh
Attorney, Agent, or Firm—Armstrong, Nikaido, Marmelstein & Kubovcik

[57] ABSTRACT

Compounds of the formula:

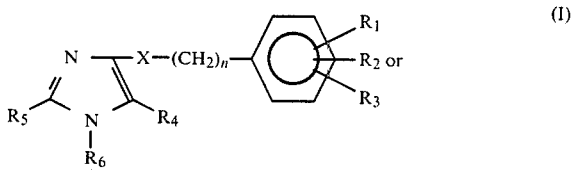

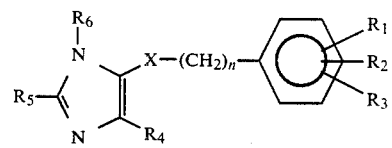

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or alkyl of 1 to 7 carbon atoms; $R_5$ is hydrogen or a straight or branched alkyl group of 1 to 5 carbon atoms or a phenyl group; and $R_6$ is hydrogen or an alkyl group of 1 to 7 carbon atoms or a substituted or unsubstituted benzyl, X is —$CH_2$—, —CHOH— or —CH=CH— and n is 0–4; provided that $R_5$ and $R_6$ are simultaneously hydrogen only when n is 4 and X is —CH=CH—; and their non-toxic pharmaceutically acceptable acid addition salts and mixtures thereof exhibit valuable pharmacological activity and are useful in the treatment of mammals, especially as antithrombotic agents. Furthermore, some of the compounds have proved to possess antihypertensive or β-blocking activity. Antimicrobial and antifungal properties have also been found. Processes for the preparation of these compounds are described, as are novel pharmaceutical compositions comprising at least one of the compounds or their salts.

29 Claims, No Drawings

SUBSTITUTED IMIDAZOLE DERIVATIVES AND THEIR USE AS ANTI-THROMBOSIS AGENTS

The present invention relates to substituted imidazole derivatives and their non-toxic, pharmaceutically acceptable acid addition salts, and their preparation, to pharmaceutical compositions containing the same, and to their use.

The imidazole derivatives of the present invention have the general formula:

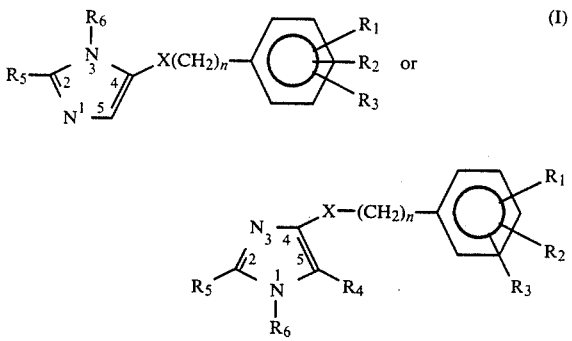

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or an alkyl radical of 1 to 7 carbon atoms; $R_5$ is hydrogen or a straight or branched alkyl group of 1 to 5 carbon atoms or a phenyl group; and $R_6$ is hydrogen or an alkyl radical of 1 to 7 carbon atoms or a substituted or unsubstituted benzyl; X is —$CH_2$, —CHOH— or —CH=CH—; and n is an integer from 0 to 4, provided that $R_5$ and $R_6$ are simultaneously hydrogen only when n is 4 and X is —CH=CH—. It will be appreciated that when $R_6$ is hydrogen the two aforesaid formulae are effectively the same. When $R_6$ is substituted benzyl it preferably carries up to 3 substituents selected from the same radicals as $R_1$, $R_2$ and $R_3$.

The non-toxic pharmaceutically acceptable acid addition salts of these compounds are also within the scope of the invention.

The compounds of formulae I are novel except for those in which n is 0, X is $CH_2$, $R_1$, $R_2$, $R_3$ and $R_6$ are all hydrogen, $R_4$ is hydrogen or ethyl, and $R_5$ is methyl or phenyl; n is 0, X is CHOH, $R_1$, $R_2$, $R_3$ and $R_4$ are all hydrogen and one or both of $R_5$ and $R_6$ is methyl; and n is 2, X is CHOH, $R_1$, $R_2$, $R_4$ and $R_5$ are all hydrogen, $R_6$ is methyl, and $R_3$ is 2-amino. No therapeutic utility has however been disclosed for the known compounds.

The compounds of the formula (I) form acid addition salts with both organic and inorganic acids. They can thus form many pharmaceutically useable acid addition salts, as, for instance, chlorides, bromides, sulfates, nitrates, phosphates, sulfonates, formates, tartrates, maleates, citrates, benzoates, salicylates, ascorbates and the like.

The invention includes within its scope pharmaceutical compositions comprising at least one of the compounds of formula (I) or a non-toxic, pharmaceutically acceptable salt thereof, and a compatible pharmaceutically acceptable carrier therefor.

The present invention provides, for example, the following specific compounds of formula (I) wherein X is —$CH_2$—:

4-(2'-methylbenzyl)-2-methylimidazole
4-(4'-methylbenzyl)-2-methylimidazole
4-(3'-methylbenzyl)-2-methylimidazole
4-(2'-chlorobenzyl)-2-methylimidazole
4-(2',6'-dimethylbenzyl)-2-methylimidazole
4-(2',3'-dimethylbenzyl)-2-methylimidazole
4-(2',5'-dimethylbenzyl)-2-methylimidazole
4-(2',6'-dichlorobenzyl)-2-methylimidazole
4-(2',6'-dimethylbenzyl)-2-ethylimidazole
4-(2'-chlorobenzyl)-2-ethylimidazole
4-(2',6'-dimethylbenzyl)-2-propylimidazole
4-(2',6'-dimethylbenzyl)-2-n-butylimidazole
4-(2',6'-dimethylbenzyl)-2-tert.butylimidazole
4-[2-(2',6'-dimethylphenyl)ethyl]-2-methylimidazole
4-[2-(2',3'-dimethylphenyl)ethyl]-2-methylimidazole
4-[3-(2'-chlorophenyl)propyl]-2-methylimidazole
4-[3-(2',6'-dimethylphenyl)propyl]-2-methylimidazole
4-[4-(2'-chlorophenyl)butyl]-2-methylimidazole
4-[4-(2',6'-dimethylphenyl)butyl]-2-methylimidazole
4-[5-(2'-chlorophenyl)pentyl]-2-methylimidazole
4-[5-(2',6'-dimethylphenyl)pentyl]-2-methylimidazole
4-[2-(2'-chlorophenyl)ethyl]-2-ethylimidazole
4-[3-(2',6'-dimethylphenyl)propyl]-2-ethylimidazole
4-[2-(3'-chlorophenyl)ethyl]-2-propylimidazole
4-[2-(2',6'-dimethylphenyl)ethyl]-2-tert.butylimidazole
4-[4-(2',6'-dimethylphenyl)butyl]-2-phenylimidazole
4-(2'-methylbenzyl)-1-methylimidazole
4-(4'-methylbenzyl)-1-methylimidazole
4-(3'-methylbenzyl)-1-methylimidazole
4-(2'-chlorobenzyl)-1-methylimidazole
4-(2',6'-dimethylbenzyl)-1-methylimidazole
4-(2',3'-dimethylbenzyl)-1-methylimidazole
4-(2',5'-dimethylbenzyl)-1-methylimidazole
4-(2',6'-dichlorobenzyl)-1-methylimidazole
4-(2',6'-dimethylbenzyl)-1-ethylimidazole
4-(2'-chlorobenzyl)-1-ethylimidazole
4-(2',6'-dimethylbenzyl)-1-propylimidazole
4-(2',6'-dimethylbenzyl)-1-n-butylimidazole
4-(2',6'-dimethylbenzyl)-1-tert.butylimidazole
4-[2-(2',6'-dimethylphenyl)ethyl]-1-methylimidazole
4-[2-(2',3'-dimethylphenyl)ethyl]-1-methylimidazole
4-[3-(2'-chlorophenyl)propyl]-1-methylimidazole
4-[3-(2',6'-dimethylphenyl)propyl]-1-methylimidazole
4-[4-(2'-chlorophenyl)butyl]-1-methylimidazole
4-[4-(2',6'-dimethylphenyl)butyl]-1-methylimidazole
4-[5-(2'-chlorophenyl)pentyl]-1-methylimidazole
4-[5-(2',6'-dimethylphenyl)pentyl]-1-methylimidazole
4-[2-(2'-chlorophenyl)ethyl]1-ethylimidazole
4-[3-(2',6'-dimethylphenyl)propyl]-1-ethylimidazole
4-[2-(3'-chlorophenyl)ethyl]-1-propylimidazole
4-[2-(2',6'-dimethylphenyl)ethyl]-1-tert.butylimidazole
4-(2',6'-dimethylbenzyl)-1-benzylimidazole
4,1-bis(2'-methylbenzyl)imidazole
4,1-bis(2',3'-dimethylbenzyl)imidazole
4,1-bis(3',4'-dimethylbenzyl)imidazole
4,1-bis(2',6'-dimethylbenzyl)imidazole
4,1-bis(2'-chlorobenzyl)imidazole
4-(2',6'-dimethylbenzyl)-3-benzylimidazole
4,3-bis(2'-methylbenzyl)imidazole
4,3-bis(2',3'-dimethylbenzyl)imidazole
4,3-bis(3',4'-dimethylbenzyl)imidazole
4,3-bis(2',6'-dimethylbenzyl)imidazole
4,3-bis(2'-chlorobenzyl)imidazole
4-(2'-methylbenzyl)-3-methylimidazole
4-(4'-methylbenzyl)-3-methylimidazole
4-(3'-methylbenzyl)-3-methylimidazole
4-(2'-chlorobenzyl)-3-methylimidazole
4-(2',6'-dimethylbenzyl)-3-methylimidazole 4-(2',3'-dimethylbenzyl)-3-methylimidazole
4-(2',5'-dimethylbenzyl)-3-methylimidazole
4-(2',6'-dichlorobenzyl)-3-methylimidazole
4-(2',6'-dimethylbenzyl)-3-ethylimidazole
4-(2'-chlorobenzyl)-3-ethylimidazole
4-(2',6'-dimethylbenzyl)-3-propylimidazole
4-(2',6'-dimethylbenzyl)-3-n-butylimidazole
4-(2',6'-dimethylbenzyl)-3-tert.butylimidazole
4-[2-(2',6'-dimethylphenyl)ethyl]-3-methylimidazole
4-[2-(2',3'-dimethylphenyl)ethyl]-3-methylimidazole
4-[3-(2'-chlorophenyl)propyl]-3-methylimidazole
4-[3-(2',6'-dimethylphenyl)propyl]-3-methylimidazole
4-[4-(2'-chlorophenyl)butyl]-3-methylimidazole
4-[4-(2',6'-dimethylphenyl)butyl]-3-methylimidazole
4-[5-(2'-chlorophenyl)pentyl]-3-methylimidazole
4-[5-(2',6'-dimethylphenyl)pentyl]-3-methylimidazole
4-[2-(2'-chlorophenyl)ethyl]-3-ethylimidazole
4-[3-(2',6'-dimethylphenyl)propyl]-3-ethylimidazole
4-[2-(3'-chlorophenyl)ethyl]-3-propylimidazole
4-[2-(2',6'-dimethylphenyl)ethyl]-3-tert.butylimidazole
4-(2',6'-dimethylbenzyl)-5-methyl-1-methylimidazole
4-(2',3'-dimethylbenzyl)-5-methyl-1-methylimidazole
4-(2'-methylbenzyl)-5-methyl-1-methylimidazole
4-[2-(2',6'-dimethylphenyl)ethyl]-2-methyl-1-methylimidazole
4-[2-(2',3'-dimethylphenyl)ethyl]-2-methyl-1-methylimidazole
4-[3-(2',6'-dimethylphenyl)propyl]-2-methyl-3-methylimidazole
4-(2',6'-dimethylbenzyl)-1-(2'-chlorobenzyl)-imidazole
4-(2',6'-dimethylbenzyl)-3-(2'-chlorobenzyl)-imidazole
4-[2-(2',6'-dimethylphenyl)ethyl]-1-(4'-methylbenzyl)-imidazole
4-[2-(2',6'-dimethylphenyl)ethyl]-3-(4'-methylbenzyl)-imidazole
4-(2',3'-dimethylbenzyl)-1-(4'-methylbenzyl)-imidazole
4-(2',3'-dimethylbenzyl)-3-(4'-methylbenzyl)-imidazole
4-(2',6'-dimethylbenzyl)-1-(3'-methylbenzyl)-imidazole
4-(2',6'-dimethylbenzyl)-3-(3'-methylbenzyl)-imidazole
4-[2-(2',6'-dimethylphenyl)ethyl]-1-(2'-methylbenzyl)-imidazole
4-[2-(2',6'-dimethylphenyl)ethyl]-1-(2',6'-dichlorobenzyl-imidazole
4-(2',3'-dimethylbenzyl)-1-(2',6'-dichlorobenzyl)-imidazole
4-(2',3'-dimethylbenzyl)-3-(2',6'-dichlorobenzyl)-imidazole
4-[2-(2',6'-dimethylphenyl)ethyl]-1-benzylimidazole
4-[5-(2',6'-dimethylphenyl)pentyl]-3-ethylimidazole
4-[2-(2',6'-dimethylphenyl)ethyl]-3-ethylimidazole The following specific compounds of formula (I) wherein X is —CHOH—;
4-[α-(2',6'-dimethylphenyl)hydroxymethyl]-2-ethylimidazole
4-[α-(2',6'-dimethylphenyl)hydroxymethyl]-2-n-butylimidazole
4-[2-(2',6'-dimethylphenyl)-1-hydroxyethyl]-2-methylimidazole
4-[α-(2',6'-dimethylphenyl)hydroxymethyl]-2-phenylimidazole
4-[α-(2',6'-dimethylphenyl)hydroxymethyl]-2-methylimidazole
4-[α-(2',3'-dimethylphenyl)hydroxymethyl]-2-methylimidazole
4-[3-(2',6'-dimethylphenyl)-1-hydroxypropyl]-2-ethylimidazole
4-[4-(2'-chlorophenyl)-1-hydroxybutyl]-2-methylimidazole
4-[4-(2',6'-dichlorophenyl)-1-hydroxybutyl]-2-methylimidazole
4-[5-(2',6'-dimethylphenyl)-1-hydroxypentyl]-2-methylimidazole
4-[α-(2',3'-dimethylphenyl)hydroxymethyl]-3-(2'-chlorobenzyl)imidazole
4-[α-(2',6'-dimethylphenyl)hydroxymethyl]-3-(3'-methylbenzyl)imidazole
4-[α-(2',3'-dimethylphenyl)hydroxymethyl]-3-benzylimidazole
4-[α-(3'-methylphenyl)hydroxymethyl]-3-benzylimidazole
4-(2-phenyl-1-hydroxyethyl)-3-benzylimidazole
4-[α-(4'-chlorophenyl)hydroxymethyl]-3-benzylidazole
4-(3-phenyl-1-hydroxypropyl)-3-benzylimidazole
4-[3-(3',4'-dimethylphenyl)-1-hydroxypropyl]-3-benzylimidazole
4-[α-(2',3'-dimethylphenyl)hydroxymethyl]-3-(4'-chlorobenzyl)imidazole
4-[α-(3'-methylphenyl)hydroxymethyl]-3-(4'-chlorobenzyl)imidazole
4-(2-phenyl-1-hydroxyethyl)-3-(4'-chlorobenzyl)imidazole
4-[α-(4'-chlorophenyl)hydroxymethyl]-3-(4'-chlorobenzyl)imidazole
4-(3-phenyl-1-hydroxypropyl)-3-(4'-chlorobenzyl)imidazole
4-[3-(3',4'-dimethylphenyl)-1-hydroxypropyl]-3-(4'-chlorobenzyl)-imidazole
4-[α-(2',3'-dimethylphenyl)hydroxymethyl]-3-(4'-methylbenzyl)imidazole
4-[α-(3'-methylphenyl)hydroxymethyl]-3-(4'-methylbenzyl)imidazole
4-(2-phenyl-1-hydroxyethyl)-3-(4'-methylbenzyl)imidazole
4-[α-(4'-chlorophenyl)hydroxymethyl]-3-(4'-methylbenzyl)imidazole
4-(3-phenyl-1-hydroxypropyl)-3-(4'-methylbenzyl)imidazole
4-[3-(3',4'-dimethylphenyl)-1-hydroxypropyl]-3-(4'-methylbenzyl)imidazole
4-[3-(2',6'-dimethylphenyl)-1-hydroxypropyl]-3-benzylimidazole
4-[2-(2',6'-dimethylphenyl)-1-hydroxyethyl]-3-benzylimidazole
4-[3-(2',6'-dimethylphenyl)-1-hydroxypropyl]-3-ethylimidazole
4-[5-(2',6'-dimethylphenyl)-1-hydroxypentyl]-3-ethylimidazole
4-[2-(2',6'-dimethylphenyl)-1-hydroxyethyl]-3-ethylimidazole and the following specific compounds of formula (I) wherein X is —CH═CH—;
4-[2-(2',6'-dimethylphenyl)ethenyl]-2-methylimidazole
4-[3-(2',6'-dimethylphenyl)-1-propenyl]-2-ethylimidazole
4-[4-(2'-chlorophenyl)-1-butenyl]-2-methylimidazole
4-[4-(2'-chlorophenyl)-1-butenyl]-2-ethylimidazole
4-[4-(2',6'-dichlorophenyl)-1-butenyl]-2-methylimidazole
4-[4-(2',4'-dichlorophenyl)-1-butenyl]-2-methylimidazole
4-[4-(2'-methylphenyl)-1-butenyl]-2-ethylimidazole
4-[4-(3'-methylphenyl)-1-butenyl]-2-ethylimidazole
4-[4-(2',6'-dimethylphenyl)-1-butenyl]-2-methylimidazole
4-[4-(2',3'-dimethylphenyl)-1-butenyl]-2-methylimidazole 4-[5-(2'-chlorophenyl)-1-pentenyl]-2-methylimidazole
4-[5-(2',6'-dichlorophenyl)-1-pentenyl]-2-ethylimidazole
4-[5-(2',4'-dichlorophenyl)-1-pentenyl]-2-ethylimidazole
4-[5-(2'-methylphenyl)-1-pentenyl]-2-methylimidazole
4-[5-(3'-methylphenyl)-1-pentenyl]-2-methylimidazole
4-[5-(2',6'-dimethylphenyl)-1-pentenyl]-2-methylimidazole
4-[5-(2',3'-dimethylphenyl)-1-pentenyl]-2-methylimidazole
4-[6-(2'-chlorophenyl)-1-hexenyl]-2-ethylimidazole
4-[6-(2',6'-dichlorophenyl)-1-hexenyl]-2-ethylimidazole
4-[6-(2',4'-dichlorophenyl)-1-hexenyl]-2-ethylimidazole
4-[6-(2'-methylphenyl)-1-hexenyl]-2-methylimidazole
4-[6-(3'-methylphenyl)-1-hexenyl]-2-methylimidazole
4-[6-(2',6'-dimethylphenyl)-1-hexenyl]-2-methylimidazole
4-[6-(2',3'-dimethylphenyl)-1-hexenyl]-2-methylimidazole
4-[4-(2'-chlorophenyl)-1-butenyl]-1-methylimidazole
4-[4-(2',6'-dimethylphenyl)-1-butenyl]-1-methylimidazole
4-[5-(2'-methylphenyl)-1-pentenyl]-1-methylimidazole
4-[5-(2',6'-dimethylphenyl)-1-pentenyl]-1-ethylimidazole
4-[6-(2'-methylphenyl)-1-hexenyl]-1-ethylimidazole
4-[6-(2',6'-dimethylphenyl)-1-hexenyl]-1-ethylimidazole
4-[4-(2'-chlorophenyl)-1-butenyl]-3-methylimidazole
4-[4-(2',6'-dimethylphenyl)-1-butenyl]-3-methylimidazole
4-[5-(2'-methylphenyl)-1-pentenyl]-3-methylimidazole
4-[6-(2',6'-dimethylphenyl)-1-hexenyl]-imidazole
4-[6-(2',6'-dimethylphenyl)-1-hexenyl]-5-methylimidazole
4-[6-(2',6'-dichlorophenyl)-1-hexenyl]-5-methylimidazole
4-[6-(2'-chlorophenyl)-1-hexenyl]-imidazole
4-[6-(2'-chlorophenyl)-1-hexenyl]-5-methylimidazole
4-[5-(2',6'-dimethylphenyl)-1-pentenyl]-3-ethylimidazole
4-[6-(2'-methylphenyl)-1-hexenyl]-3-ethylimidazole
4-[6-(2',6'-dimethylphenyl)-1-hexenyl]-3-ethylimidazole
4-[2-(2',6'-dimethylphenyl)ethenyl]-3-benzylimidazole
4-[3-(2',6'-dimethylphenyl)-1-propenyl]-3-benzylimidazole
4-[2-(2',6'-dimethylphenyl)ethenyl]-3-ethylimidazole
4-[3-(2',6'-dimethylphenyl)-1-propenyl]-3-ethylimidazole The compounds of the present invention have been found to possess excellent antithrombotic activity. Preliminary tests have shown that they also possess other valuable pharmacological properties, for example, antihypertensive and β-blocking effects. Antimicrobial and antifungal properties have also been found.

While all of the compounds of formula (I) have the aforementioned activities, certain groups of compounds remain preferred. One such preferred group can be represented by the structural formula:

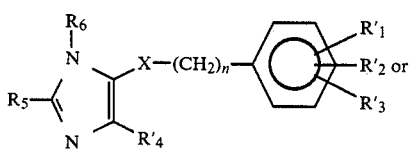
(II)

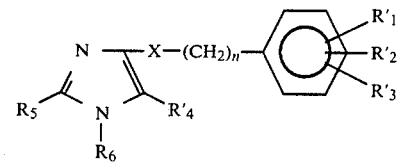

wherein n and $R_5$ and $R_6$ are the same as before; each of $R'_1$, $R'_2$ and $R'_3$, is hydrogen, chloro, methyl, ethyl, methoxy or hydroxy; and $R'_4$ is hydrogen, methyl or ethyl. Preferably at least one of $R'_1$, $R'_2$ and $R'_3$ is other than hydrogen.

According to a feature of the invention, the compounds of formula (I) in which X is —CHOH— are made by a Grignard reaction in which an imidazole aldehyde of the formula:

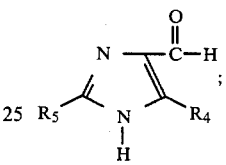

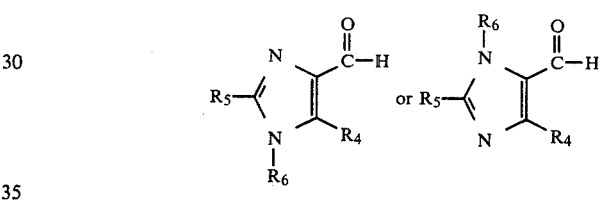

wherein $R_4$, $R_5$ and $R_6$ are as defined before, is reacted with an arylalkyl magnesium halide derivative of the formula:

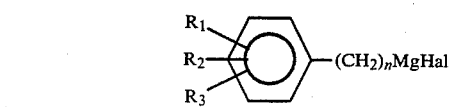

wherein $R_1$, $R_2$, $R_3$ and n are as defined before and Hal is a halogen atom.

The arylalkylmagnesium halide derivative can be, for example, an arylalkylmagnesiumbromide derivative, which is prepared by reacting the corresponding arylalkylbromide derivative with magnesium. Suitable solvents for the reaction include a variety of ethers, preferably tetrahydrofura. The arylalkylmagnesiumhalide derivative is prepared in the usual way by adding the arylalkylmagnesiumhalide derivative in a suitable solvent, e.g. tetrahydrofuran, dropwise onto magnesium turnings covered by tetrahydrofuran, at the boiling point of the reaction mixture. When the magnesium turnings have reacted, the mixture is cooled slightly and the 4-imidazole derivative is added in solid form in small portions. After the addition, the reaction mixture is refluxed until all of the 4-imidazole derivative has reacted. The reaction time varies between one and five hours.

It is surprising that in the above described Grignard reaction a compound of the formula (III)

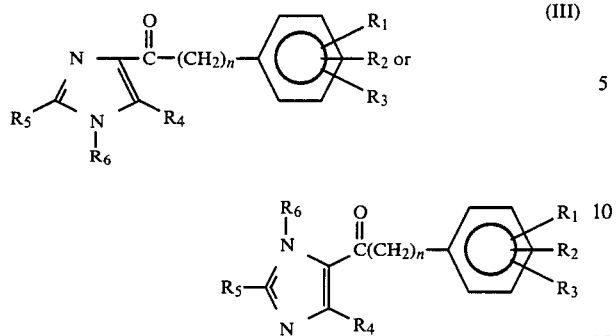

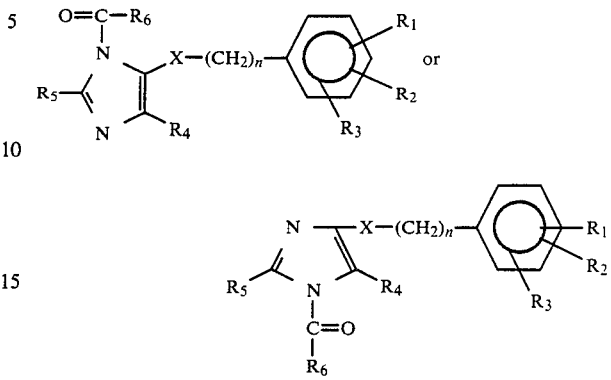

wherein $R_1$, $R_2$, $R_3$, $R_4$, $R_5$, $R_6$ and n are the same as before, is formed. The amount of the compounds of the formula (III), which can be isolated from the reaction mixture depends on the structure of the derivatives, the reaction time, and the amount of Grignard reagent used. Thus when one and a half equivalents of a longer chained Grignard reagent are reacted with the aldehyde derivative using relatively shorter reaction times than usually, from about one half to two hours, the amount of the compound of formula (III) can be as high as 50% of the isolated products.

Another process for the preparation of compounds of the present invention, in which X is —CHOH— comprises reducing a compound of the formula (III) to a compound of formula (I) wherein X is —CHOH—. The reduction is performed by usual methods, for example using sodium borohydride in ethanol.

A two-stage process for the preparation of compounds of the present invention wherein X is —CH$_2$— comprises a first stage wherein a compound of the formula (I) in which X is —CHOH— is dehydrated to a compound of the formula (IV)

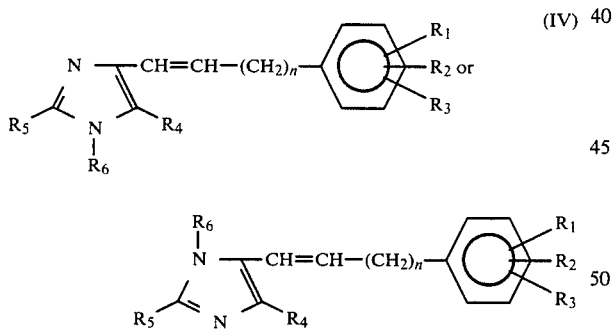

wherein $R_1$, $R_2$, $R_3$, $R_4$, $R_5$, $R_6$ and n are defined as before, and a second stage, wherein the compound of the formula (IV) is hydrogenated to a compound of the formula (I) in which X is —CH$_2$—.

The dehydration is preferably performed by refluxing in an appropriate acidic solution, e.g. concentrated hydrochloric acid or heating for example with potassium hydrogen sulfate. In the second stage the hydrogenation is conveniently carried out at room temperature with good stirring in the above mentioned acidic solution in the presence of a catalyst in a hydrogen atmosphere. Suitable catalysts are for example platinum oxide, palladium-on-carbon or Raney-nickel.

A further process for the preparation of the compounds of the formula (I) in which X is —CH$_2$— comprises hydrolysing a corresponding compound of the formula:

prises hydrolysing a corresponding compound of the formula:

wherein $R_1$, $R_2$, $R_3$, $R_4$, $R_5$, $R_6$ and n are as defined before. Preferably, the hydrolysis is carried out by boiling the starting material, an N-acylated imidazole derivative, in an aqueous solution of an inorganic acid until the reaction is completed.

Yet another process for the preparation of the compounds of formula (I) in which X is —CH$_2$— or CHOH, comprises hydrogenating a starting material of the formula:

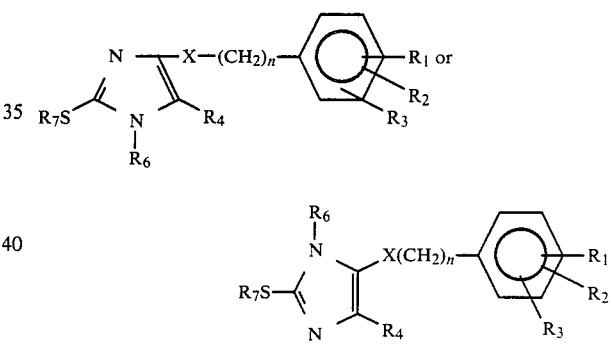

wherein $R_1$, $R_2$, $R_3$, $R_4$, $R_5$, $R_6$ and n are as defined before and $R_7$ is an alkyl or an aryl group. The hydrogenation is conveniently conducted in the presence of a suitable catalyst and under a hydrogen atmosphere, with stirring. Suitable catalysts include platinum oxide, palladium-on-carbon and Raney nickel. Reaction temperatures vary with the particular starting material employed, with typical temperatures being 25°-70° C.

Yet another process for the preparation of the compounds of formula (I), wherein X is —CH$_2$— or CHOH, comprises hydrogenation of the benzyl group $R_8CH_2$— of a starting material of the formula:

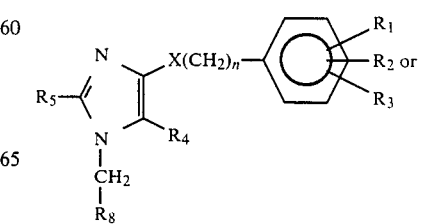

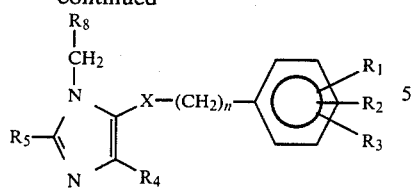

wherein $R_1$, $R_2$, $R_3$, $R_4$, $R_5$ and n are as defined before and $R_8$ is a substituted or an unsubstituted phenyl group. The hydrogenation is conveniently conducted in liquid ammonia with sodium at a lowered temperature.

The present invention further provides yet another process for preparing compounds of the invention in which X is —$CH_2$—. Thus, according to this embodiment of the invention, a starting material of the formula V:

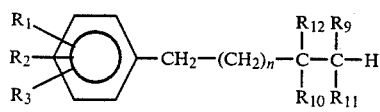

wherein $R_1$, $R_2$, $R_3$ and n are as hereinbefore defined; wherein $R_9$, $R_{10}$, $R_{11}$ and $R_{12}$, which can be the same or different, are each hydrogen, or alkyl of 1 to 7 carbon atoms, hydroxy, halogen, amino, —O— alkyl of 1 to 7 carbon atoms or

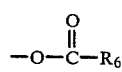

wherein $R_6$ is defined as before; or wherein $R_{12}$ and $R_{10}$ can be combined to form a keto group, or $R_9$ and $R_{11}$ can be combined to form a keto group, or both $R_{12}$ and $R_{10}$ and $R_9$ and $R_{11}$ can simultaneously form keto groups; is reacted with a reagent capable of converting said starting material to the corresponding imidazole of the formula:

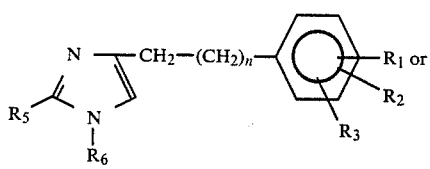

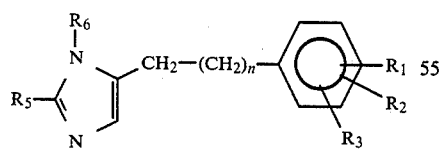

wherein $R_1$, $R_2$, $R_3$ and n are defined as before. Reagents capable of converting the depicted starting material to the corresponding imidazole include

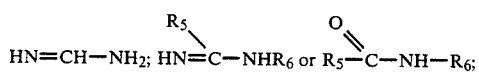

wherein $R_5$ and $R_6$ are as before.

A surprising aspect of the above mentioned reaction is the fact that the hydroxyacetal starting materials, e.g., compounds of the formula:

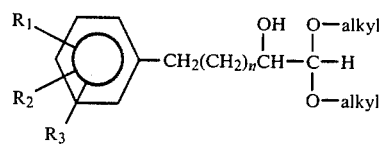

react with

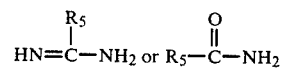

to form the corresponding imidazoles.

Yet another method for the preparation of the compounds of formula (I) wherein X is —$CH_2$— comprises reacting a N-trialkylsilylimidazole of the formula

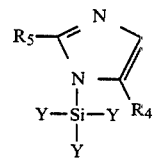

wherein Y is an alkyl group, preferably methyl, with an arylalkylhalogenide of the formula

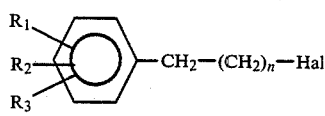

wherein $R_1$, $R_2$, $R_3$ and n are as before and Hal is a halogen atom, in the presence of a Lewis acid, for example titanium tetrachloride, aluminium chloride or zinc chloride. As solvent can be used for example methylene chloride or chloroform. The reaction is preferably carried out at room temperature stirring the starting materials for 6-12 hours.

According to a feature of the invention, the compounds of formula (I) wherein X is —CH=CH—, are prepared, by dehydration of the corresponding imidazoles of the formula:

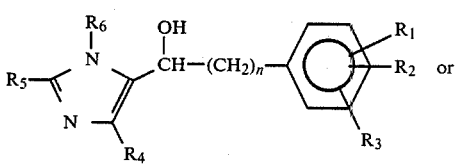

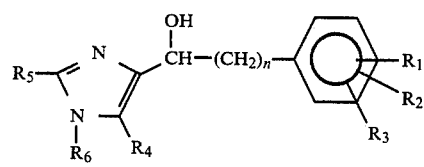

wherein $R_1$, $R_2$, $R_3$, $R_4$, $R_5$ and $R_6$ are defined as before and n is 1-5. The dehydration is carried out according to known methods for instance by refluxing the hydroxysubstituted compound in an appropriate acidic solution, e.g. concentrated hydrochloric acid. Alternatively the hydroxysubstituted imidazole can be dehydrated by heating it together with anhydrous potassium hydrogen sulfate.

Another process for the preparation of compounds of formula (I), wherein X is —CH=CH—, is a Wittig reaction which comprises reacting an imidazole aldehyde of the formula:

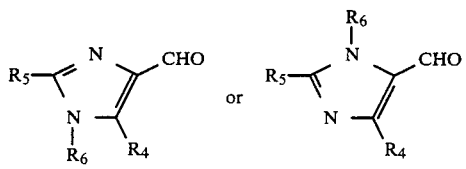

wherein $R_4$, $R_5$ and $R_6$ are the same as before, with an aralkylidenetriphenylphosphorane of the formula:

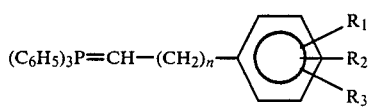

wherein $R_1$, $R_2$ and $R_3$ are the same as before and n is 0–4. The aralkylidenetriphenylphosphoranes are preferably prepared by reacting the corresponding aralkyltriphenylphosphonium halide of the formula:

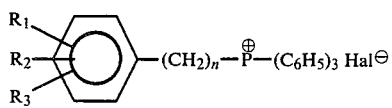

wherein $R_1$, $R_2$ and $R_3$ are the same as before, n is 0–5 and Hal is a halogen atom, with a basic reagent, preferably butyllithium.

The processes described above for the preparation of compounds of formula (1), wherein X is —CH=CH—, result mainly in the trans isomer of the compound. The trans isomer can be converted to the cis isomer according to known methods, e.g. by heating it in the presence of an acid or by irradiating it with ultraviolet light.

A method for the preparation of compounds of formula (I) wherein $R_6$ is an alkyl of 1 to 7 carbon atoms or benzyl, comprises alkylation of a compound of the formula

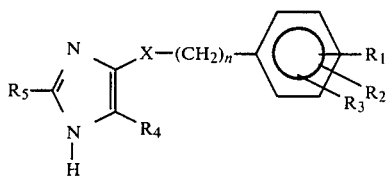

wherein $R_1$, $R_2$, $R_3$, $R_4$, $R_5$, X and n are as defined before with a compound of the formula

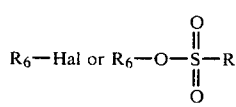

wherein $R_6$ is an alkyl group of 1 to 7 carbon atoms or a substituted or unsubstituted benzyl, Hal is a halogen atom and R is a sulphuric acid residue, for example p-tolyl.

The alkylation can be performed for example by reacting an alkylhalide or an alkyltosylate in dimethylformamide in the presence of sodium hydride with the starting imidazole. From the mixture obtained containing 1—$R_6$— and 3—$R_6$—imidazole derivative, the components can be separated for example by crystallization or column chromatographically.

The alkylation can also be performed as a phase-transfer reaction through the reaction of the starting imidazole derivatives with the alkylhalide or the alkyltosylate in the presence of a phase transfer reagent, for example triphenylbenzylammoniumchloride or tetrabutylammoniumhydrogensulfate in an alkaline water solution.

Another method for the preparation of compounds of formula (I) wherein $R_6$ is an alkyl group of 1–7 carbon atoms or a substituted or unsubstituted benzyl, $R_5$ is hydrogen and X is —$CH_2$—, is a so-called TosMIC reaction. (TosMIC = p-toluenesulfonylmethylisocyanide). This method gives specific isomers of the formula

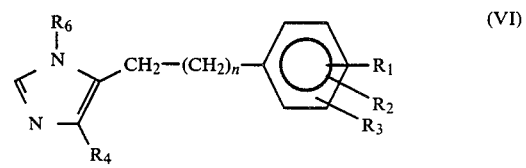

(VI)

wherein $R_1$, $R_2$, $R_3$, $R_4$, $R_6$ and n are as before.

This method comprises reacting a p-toluenesulfonylmethylisocyanide compound of the formula

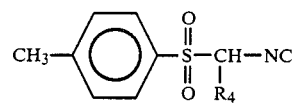

wherein $R_4$ is as defined before, with a primary amine of the formula $R_6NH_2$ and an aldehyde of the formula

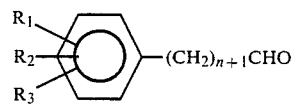

or with an imine of the formula

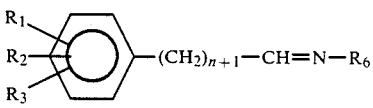

wherein $R_1$, $R_2$, $R_3$, $R_6$ and n are as before, to give the corresponding imidazole of the formula

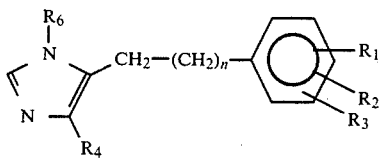

The reaction is carried out in an alkaline solution of methanol or dimethoxyethane. The reaction is performed either with an excess of primary amine or in the presence of sodium carbonate or potassium carbonate. The temperature ranges from room temperature to the boiling point of the solvent.

As stated herein above, the compounds of the general formula (I) and their non-toxic, pharmaceutically acceptable acid addition salts have valuable pharmacological properties and have been found to possess excellent antithrombotic properties.

Tests have shown that they also possess other pharmacological properties as well, for example, antihypertensive and $\beta$-blocking activity. Furthermore, antimicrobial and antifungal properties have been found, too.

Administration of isomeric compounds of formula (I), their non-toxic, pharmaceutically acceptable acid salts or mixtures thereof may be achieved parenterally, intravenously or orally. Typically, an effective amount of the derivative is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc., and of course the structure of the derivative.

The pharmaceutical carriers which are typically employed with the derivatives of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The clinical dosage ranges for the compounds of the invention have been estimated for oral administration antithrombotic and antihypertensive agents, 0.2 to 2 mg/kg per day and antimicrobial agents 0.3 to 3 mg/kg per day.

Acute toxicity ($LD_{50}$) ranges from 15 to 100 mg/kg i.v. in mice for the tested compounds.

The anti-hypertensive properties of the imidazole derivatives of the present invention have been determined by the following procedure. Sprague-Dawley rats of normal weight were first anesthetized with urethane. After this, the femoral artery was connected by way of a polyethylene tube with a blood pressure transducer. The test substance was then injected into the femoral vein and the blood pressure and the pulse frequency were registered with a recorder.

The antithrombotic activity was investigated in vitro. The inhibiting activity of the compounds against ADP- and collagen-induced aggregation of thrombocytes was measured. In the test thrombocytes from a cow were used. To 1.2 ml of plasma containing 250000 thrombocytes/mm$^3$ were added 50 $\mu$l of a solution of the compound to be tested. After 10 min incubation either ADP or collagen was added. The aggregation of the thrombocytes was turbidimetrically determined at $\lambda = 605$ n m.

The antimicrobial activity was determined in vitro according to a qualitative test for antibacterial and antifungal activity, using the agar diffusion method, against the following standard organisms: *Staphylococcus aureus, Streptococcus pyogenes, Escherichia coli, Proteus mirabilis, Pseudomonas aeruginosa, Candida albicans* and *Aspergillus niger.*

The antimycotic activity was determined in vitro against the following dermatophytes and fungi species: *Trichophyton rubrum, Trichophyton mentagrophytes, Microsporum canis, Epidermophyton floccosum, Chrysosporum, Candida albicans, Candida guilliermondi, Candida parapsilosis, Torulopsis glabrata* and *Saccharomyces cerevisiae.* The fungi were cultured by plating on an agar nutrient medium. The compound to be tested was added before the incubation. A measure of the efficiency of te compound tested is the radius of the circle, within which the growth of the fungi has been inhibited.

The $\beta$-blocking activity was measured in vitro as follows: The attrium of a guinea-pig was isolated. The inhibiting activity of the compound against isoprenaline-induced chronotropic and inotropic action in the isolated atrium was measured.

Acute toxicity was determined by using female mice of NMRI-Strain with an age of about 7 months and weighing 30–40 g. The administration of the test compound was i.v.

In the antithrombotic activity test, the compound 4-(2',6'-dimethylbenzyl)-2-methylimidazole, which has a $LD_{50}$ of 15 mg/kg i.v. in mice, inhibited the collagen-induced and the ADP-induced aggregation of thrombocytes clearly.

In the same test, all the following compounds inhibited the collagen-induced and the ADP-induced aggregation of thrombocytes effectively:

4-(2',6'-dimethylbenzyl)-2-ethylimidazole
4-(2',6'-dimethylbenzyl)-2-n-butylimidazole
4-[3-(2',6'-dimethylphenyl)-1-hydroxypropyl]-2-ethylimidazole
4-[2-(2',6'-dimethylphenyl)-1-hydroxyethyl]-3-benzylimidazole
4-[3-(2',6'-dimethylphenyl)-1-hydroxypropyl]-3-benzylimidazole
4-[5-(2',6'-dimethylphenyl)-1-hydroxypentyl]-3-ethylimidazole
4-[3-(2',6'-dimethylphenyl)-1-hydroxypropyl]-3-ethylimidazole
4-[5-(2',6'-dimethylphenyl)pentyl-3-ethylimidazole
4-[3-(2',6'-dimethylphenyl)propyl]-3-ethylimidazole In the antihypertensivity test, the compound 4-(2',6'-dimethylbenzyl)-2-methylimidazole caused at a dose of 0.1–3 mg/kg about 25 percent lowering of the blood pressure measured 20 minutes after administration. At the same dose the pulse frequency decreased with about 30 percent.

For example the following compounds proved to possess antihypertensive activity, too:

4-[2-(2',6'-dimethylphenyl)ethyl]-2-methylimidazole
4-(2',6'-dimethylbenzyl)-3-methylimidazole
4-(2',6'-dimethylbenzyl)-3-ethylimidazole In the antimicrobial tests for example the following compounds were active against all the species:
4-[3-(2',6'-dimethylphenyl)-1-propenyl]-2-ethylimidazole
4-[4-(2',6'-dichlorophenyl)-1-butenyl]-2-methylimidazole
4-[5-(2',6'-dimethylphenyl)-1-pentenyl]-2-methylimidazole
4-[6-(2',6'-dimethylphenyl)-1-hexenyl]-5-methylimidazole
4-[6-(2',6'-dimethylphenyl)-1-hexenyl]-imidazole
4-[6-(2'-chlorophenyl)-1-hexenyl]-imidazole
4-[6-(2',6'-dichlorophenyl)-1-hexenyl]-5-methylimidazole
4-[6-(2'-chlorophenyl)-1-hexenyl]-5-methylimidazole In the Examples below, where $I_H$-NMR spectrum shifts are presented, the NMR spectra were determined with a Perkin-Elmer R 24 apparatus using an external tetramethylsilane standard, from which the presented chemical shifts (δ,ppm) are tabulated. The letters s, d, t and m are used to indicate a singlet, doublet, triplet or multiplet, respectively. In the same connection, the number of hydrogen atoms is also stated. The compounds which are indicated as bases are tested in deuterium methanol, deuterium acetone or deuterium chloroform, while the values for compounds which are indicated as hydrochlorides were determined in deuterium oxide. The presented $^{13}$C-NMR-spectrum were determined with a Bruker WB-80 DS apparatus.

The following Examples illustrate the invention.

EXAMPLE 1

4-[α-(2',6'-dimethylphenyl)-hydroxymethyl]-2-ethylimidazole 6.12 g of dry magnesium turnings are covered with 100 ml of dry tetrahydrofuran (THF). The mixture is heated to boiling and a solution of 46.7 g of 1-bromo-2,6-dimethylbenzene in 100 ml of dry tetrahydrofuran is added dropwise at such a rate that gentle refluxing is maintained. After the addition is complete, the reaction mixture is refluxed for an additional 30 minutes. The reaction mixture is cooled to 50° C. and 10.45 g of 2-ethyl-4-imidazolealdehyde is added slowly in small portions. After the addition is complete, the mixture is refluxed for 4 hours. Then the reaction mixture is cooled and poured into 200 ml of cold water containing 20 ml of concentrated hydrochloric acid. Part of the tetrahydrofuran is distilled off to give a smaller volume and the tetrahydrofuran is replaced with water. The mixture is washed twice with 50 ml portions of chloroform. The aqueous layer is made alkaline with sodium hydroxide solution (pH about 8). The precipitate which forms is washed with water and added to 100 ml of 4N NaOH solution and the mixture is stirred vigorously for one hour. The precipitate is filtered, washed several times with water and dried. The crude product is recrystallized from a mixture of water and ethanol to give 7.8 g of a product melting at 164°–166° C.

$^1$H-NMR: 1.25 (t, 3H), 2.33 (s, 6H), 2.681 (q, 2H), 4.86 (s, 1H+H$_2$O), 6.22 (s, 1H), 6.36 (s, 1H), 7.00 (s, 3H)

$^{13}$C-NMR: 13.25 (q, 1C), 20.91 (q, 2C), 22.36 (t, 1C), 67.49 (d, 1C), 118.17 (d, 1C), 128.25 (s, 2C), 129.95 (d, 2C), 138.06 (d, 1C), 139.03 (s, 1C), 139.33 (s, 1C), 151.321 (s, 1C).

EXAMPLE 2

4-[α-(2',6'-dimethylphenyl)hydroxymethyl]-2-n-butylimidazole

The procedure of example 1 is repeated except that 2-n-butyl-4-imidazolealdehyde is used in place of 2-ethyl-4-imidazolealdehyde. M.p. of the base 152°–156° C.

EXAMPLE 3

4-[2-(2',6'-dimethylphenyl)-1-hydroxyethyl]-2-methylimidazole

The procedure of example 1 is repeated except that 2-methyl-4-imidazolealdehyde and 2,6-dimethylphenyl-bromomethane are used as starting materials.

$^1$H-NMR: 2.27 (s, 6H), 2.35 (s, 3H), 3.16 (m, 2H), 4.68 (m, 2H), 6.65 (s, 1H), 6.98 (s, 3H)

EXAMPLE 4

4-[α-(2',6'-dimethylphenyl)hydroxymethyl]-2-phenylimidazole

The procedure of example 1 is repeated except that 2-phenyl-4-imidazolealdehyde is used. M.p. of the base is 181°–183° C.

$^1$H-NMR: 2.37 (s, 6H), 4.96 (s, 1H+H$_2$O), 6.34 (d, 1H), 6.80 (d, 1H), 7.02 (s, 3H), 7.35 (m, 3H), 7.86 (m, 2H)

EXAMPLE 5

4-[α-(2',6'-dimethylphenyl)hydroxymethyl]-2-methylimidazole

The procedure of example 1 is repeated except that 2-methyl-4-imidazolealdehyde is used. M.p. of the base is 176°–177° C.

EXAMPLE 6

4-[α-(2',3'-dimethylphenyl)hydroxymethyl]-2-methylimidazole

The procedure of example 1 is repeated except that 2-methyl-4-imidazolealdehyde and 2,3-dimethyl-1-bromobenzene are used as starting materials. M.p. of the base is 176°–178° C.

According to the same method, for example the following compounds were prepared:
4-[3-(2',6'-dimethylphenyl)-1-hydroxypropyl]-2-ethylimidazole, M.p. of the base 186°–187° C.
4-[4-(2'-chlorophenyl)-1-hydroxybutyl]-2-methylimidazole, M.p. of the hydrochloride 134°–136° C.
4-[4-(2',6'-dichlorophenyl)-1-hydroxybutyl]-2-methylimidazole, M.p. (hydrochloride) 150°–151° C.
4-[5-(2',6'-dimethylphenyl)-1-hydroxypentyl]-2-methylimidazole, M.p. (base) 112°–115° C.
4-[6-(2',6'-dimethylphenyl)-1-hydroxyhexyl]-imidazole, M.p. (hydrochloride) 106°–111° C.
4-[6-(2',6'-dimethylphenyl)-1-hydroxyhexyl]-2-methylimidazole $^{13}$C-NMR (peaks ppm): 13.521, 19.969, 26.689, 30.322, 30.534, 31.079, 38.079, 38.102, 68.495, 117.234, 126.346, 128.980, 136.639, 140.392, 141.179, 145.539

4-[α-(2',3'-dimethylphenyl)hydroxymethyl]-3-benzylimidazole, M.p. of the base 129°–130,5° C.

$^1$H-NMR: 1.74 (s, 3H), 2.21 (s, 3H), 5.17 (q, 2H), 5.67 (s, 1H), 6.3 (s, 1H), 7.0–7.4 (m, 9H)

$^{13}$C-NMR: 14.38, 20.37, 49.07, 64.72, 123.75, 125.42, 127.05, 127.99, 128.84, 128.84, 129,20, 129.32, 133.44, 136.26, 136.62, 138.80, 139.22

4-[α-(3'-methylphenyl)hydroxymethyl]-3-benzylimidazole, M.p. of the base 128°–131° C.

$^1$H-NMR: 2.25 (s, 3H), 5.02 (q, 2H), 5.59 (s, 1H), 6.50 (s, 1H), 6.9–7.3 (m, 9H), 7.22 (d, 1H)

4-[α-(benzyl)hydroxymethyl]-3-benzylimidazole, M.p. of the base 156°–160° C.

$^1$H-NMR: 3.06 (d, 2H), 4.72 (t, 1H), 5.07 (s, 2H), 6.9–7.4 (m, 12H)

4-[α-(4'-chlorophenyl)hydroxymethyl]-3-benzylimidazole, M.p. of the base 160°–163° C.

$^1$H-NMR: 5.12 (q, 2H), 5.61 (s, 1H), 6.54 (s, 1H), 6.9–7.4 (m, 10H)

4-(3-phenyl-1-hydroxypropyl)-3-benzylimidazole, M.p. of the base 147°–151° C.

$^1$H-NMR: 1.9–2.3 (m, 2H), 2.5–2.8 (m, 2H), 4.48 (t, 1H), 5.16 (s, 2H), 6.92 (s, 1H), 7.00–7.35 (m, 10H), 7.37 (s, 1H)

4-[3-(3',4'-dimethylphenyl)-1-hydroxypropyl]-3-benzylimidazole, M.p. of the hydrochloride 152.5°–155° C.

$^1$H-NMR (hydrochloride): 1.9–2.2 (m, 2H), 2.19 (s, 6H), 2.55–2.75 (m, 2H), 4.60 (t, 1H), 4.95 (s, 2H), 5.48 (s, 2H), 6.75–7.10 (m, 3H), 7.1–7.5 (m, 5H), 7.54 (s, 1H), 8.99 (s, 1H)

4-[α-(2',3'-dimethylphenyl)hydroxymethyl]-3-(4'-chlorobenzyl)-imidazole, M.p. of the hydrochloride 204°–209° C.

$^1$H-NMR (hydrochloride): 1.87 (s, 3H), 2.26 (s, 3H), 4.57 (s, 2H), 5.54 (s, 2H), 5.86 (s, 1H), 6.74 (s, 1H), 7.1–7.5 (m, 7H), 9.08 (d, 1H)

4-[α-(3'-methylphenyl)hydroxymethyl]-3-(4'-chlorobenzyl)-imidazole, M.p. of the hydrochloride 179°–182° C.

$^1$H-NMR: 2.31 (s, 3H), 4.55 (broad signal, 2H), 5.41 (s, 2H), 5.78 (s, 1H), 6.98 (s, 1H), 7.0–7.4 (m, 8H), 8.86 (d, 1H)

4-(2-phenyl-1-hydroxyethyl)-3-(4'-chlorobenzyl)-imidazole, M.p. of the base 184°–188° C.

$^1$H-NMR: 3.04 (d, 2H), 4.36 (s, 2H), 4.70 (t, 1H), 5.21 (s, 2H), 6.9–7.4 (m, 10H), 7.66 (s, 1H)

4-[α-(4'-chlorophenyl)hydroxymethyl]-3-(4'-chlorobenzyl)-imidazole, M.p. of the hydrochloride 189°–195° C.

$^1$H-NMR (hydrochloride): 4.58 (board signal, 2H), 5.47 (s, 2H), 5.84 (s, 1H), 6.97 (q, 1H), 7.2–7.5 (m, 8H), 8.90 (s, 1H)

4-(3-phenyl-1-hydroxypropyl)-3-(4'-chlorobenzyl)-imidazole, M.p. of the base 135°–137° C.

$^1$H-NMR: 1.9–2.3 (m, 2H), 2.6–2.8 (m, 2H), 4.42 (t, 1H), 5.10 (s, 2H), 6.85 (d, 1H), 6.9–7.3 (m, 10H)

4-[3-(3',4'-dimethylphenyl)-1-hydroxypropyl]-3-(4'-chlorobenzyl)imidazole, M.p. of the base 126°–130° C.

$^1$H-NMR: 1.8–2.3 (m, 2H), 2.20 (s, 6H), 2.5–2.8 (m, 2H), 4.35 (broad signal, 1H), 5.11 (s, 2H), 6.7–7.4 (m, 9H)

4-[α-(2',3'-dimethylphenyl)hydroxymethyl]-3-(4'-methylbenzyl)-imidazole, M.p. of the hydrochloride 185°–190° C.

$^1$H-NMR: 1.78 (s, 3H), 2.20 (s, 3H), 2.33 (s, 3H), 5.42 (s, 2H), 5.6 (board signal, 1H), 5.99 (s, 1H), 6.63 (s, 1H), 7.0–7.4 (m, 7H), 8.72 (d, 1H)

4-[α-(3'-methylphenyl)hydroxymethyl]-3-(4'-methylbenzyl)-imidazole, M.p. of the hydrochloride 152°–155° C.

$^1$H-NMR (hydrochloride): 2.30 (s, 3H), 2.33 (s, 3H), 5.1 (board signal, 1H), 5.31 (s, 2H), 5.85 (s, 1H), 6.96 (s, 1H), 7.12 (s, 8H), 8.52 (s, 1H)

4-(2-phenyl-1-hydroxyethyl)-3-(4'-methylbenzyl)-imidazole, M.p. of the base 177°–180° C.

$^1$H-NMR: 2.33 (s, 3H), 3.08 (d, 2H), 4.75 (t, 1H), 5.04 (s, 2H), 6.8–7.5 (m, 10H)

4-[α-(4'-chlorophenyl)hydroxymethyl]-3-(4'-methylbenzyl)-imidazole, M.p. of the hydrochloride 199°–202° C.

$^1$H-NMR: 2.34 (s, 3H), 4.89 (s, 2H), 5.43 (s, 2H), 5.88 (d, 1H), 7.17 (s, board, 5H), 7.35 (s, 4H), 8.90 (d, 1H)

4-(3-phenyl-1-hydroxypropyl)-3-(4'-methylbenzyl)-imidazole, M.p. of the hydrochloride 156°–159° C.

$^1$H-NMR: 1.8–2.3 (m, 2H), 2.3 (s, 3H), 2.5–2.8 (m, 2H), 4.5–4.8 (m, 1H), 5.42 (s, 2H), 7.0–7.4 (m, 10H), 8.7 (d, 1H)

4-[3-(3',4'-dimethylphenyl)-1-hydroxypropyl]-3-(4'-methylbenzyl)imidazole, M.p. of the hydrochloride 159°–163° C.

$^1$H-NMR: 1.8–2.3 (m, 2H), 2.23 (s, 6H), 2.35 (s, 3H), 2.5–2.7 (m, 2H), 4.5 (broad signal, 1H), 4.6–4.7 (m, 1H), 5.40 (s, 2H), 6.7–7.4 (m, 8H), 8.74 (d, 1H)

4-[3-(2',6'-dimethylphenyl)-1-hydroxypropyl]-3-benzylimidazole, M.p. of the hydrochloride 148°–151° C.

$^1$H-NMR: 1.75–2.10 (m, 2H), 2.24 (s, 6H), 2.6–3.0 (m, 2H), 4.74 (t, 1H), 4.94 (s, 2H), 5.57 (s, 2H), 6.93 (s, 3H), 7.37 (s, 5H), 7.56 (s, 1H), 9.01 (d, 1H)

4-[2-(2',6'-dimethylphenyl)-1-hydroxyethyl]-3-benzylimidazole, M.p. of the base 184°–187° C.

$^{13}$C-NMR: 20.19 (2C), 37.42, 49.28, 65.33, 126.63, 127.08, 127.48, 128.57, 128.87, 129.48, 135.35, 135.89, 137.13, 138.01, 138.83

4-[3-(2',6'-dimethyl)-1-hydroxypropyl]-3-ethylimidazole, M.p. of the hydrochloride 178°–179° C.

$^{13}$C-NMR (hydrochloride): 15.76, 19.95 (2C), 26.70, 36.00, 43.84, 64.67, 117.66, 126.78, 129.08, 136.23, 136.96, 138.60, 139.00

4-[5-(2',6'-dimethylphenyl)-1-hydroxypentyl]-3-ethylimidazole. M.p. of the hydrochloride 117°–120° C.

$^{13}$C-NMR (hydrochloride): 15.77, 19.95 (2C), 27.215, 30.03, 30.45, 36.45, 43.80, 64.60, 117.70, 126.42, 128.96, 136.20, 136.68, 138.71, 140.10

4-[2-(2',6'-dimethylphenyl)-1-hydroxyethyl]-3-ethylimidazole. M.p. of the base 185°–189° C.

$^1$H-NMR: 1.28 (t, 3H), 2.23 (s, 6H), 2.8–3.4 (m, 2H), 3.91 (q, 2H), 4.6–4.85 (m, 1H), 6.85 (s, 1H), 6.97 (s, 3H), 7.58 (s, 1H)

EXAMPLE 7

4-(2',6'-dimethylbenzyl)-2-ethylimidazole 5.0 g of 4-[α-(2',6'-dimethylphenyl)hydroxymethyl]-2-ethylimidazole are dissolved in 50 ml of 4N HCl solution. About 0.5 g of 10% palladium-on-carbon (Pd/C) are added and the mixture is stirred vigorously under a hydrogen atmosphere at about 50° C. until no more hydrogen is consumed (about 4 hours). The catalyst is filtered off, the solution is made alkaline after which the product is filtered off and washed with water. Thus 4.3 g of crude base is obtained. Its melting point is 160°–163° C. The base may be converted into the hydrochloride in isopropanol-HCl-ethylacetate. M.p. of the hydrochloride is 198°–203° C.

$^1$H-NMR: 1.51 (t, 3H), 2.38 (s, 6H), 3.11 (q, 2H), 4.14 (s, 2H), 6.71 (s, 1H), 7.22 (s, 3H)

$^{13}$C-NMR: 12.99 (q, 1C), 21.34 (q, 2C+t, 1C), 26.82 (t, 1C), 116.76 (d, 1C), 129.57 (s, 2C), 130.47 (d, 2C), 133.68 (s, 1C), 135.35 (s, 1C), 139.56 (d, 1C), 151.03 (s, 1C)

EXAMPLE 8

4-(2',6'-dimethylbenzyl)-2-n-butylimidazole

The procedure of example 7 is repeated except that 4-[α-(2',6'-dimethylphenyl)hydroxymethyl]-2-n-butylimidazole is used. M.p. of the hydrochloride is 109°–116° C.

$^1$H-NMR: 0.7–1.8 (m, 7H), 2.26 (s, 6H), 2.9 (t, 2H), 3.99 (s, 2H), 6.66 (s, 1H), 7.08 (s, 3H)

In the same way was prepared for example the compound 4-[3-(2',6'-dimethylphenyl)propyl]-2-ethylimidazole, M.p. of the base 56°–61° C.

EXAMPLE 9

4-[2-(2',6'-dimethylphenyl)ethenyl]-2-methylimidazole 2.6 g of 4-[2-(2',6'-dimethylphenyl)-1-hydroxyethyl]-2-methylimidazole is mixed with 13.0 g of anhydrous potassium hydrogen sulfate and the mixture is warmed at 140° C. for 8 hours. The mixture is then cooled and methanol is added. The mixture is stirred and filtered. The product (base) is extracted in chloroform (pH 12), washed with water and dried over $Na_2SO_4$. The product obtained (2.2 g) is the crude base, which may be converted to the hydrochloride with HCl-ethylacetate is diisopropylether. The yield is 0.7 g. M.p. of the hydrochloride is 194°–197° C.

$^1$H-NMR: 2.43 (s, 6H), 2.72 (s, 3H), 6.48 (d, 1H), 7.15 (s, 3H), 7.25 (d, 1H), 7.28 (s, 1H)

According to the same method, for example the following compounds were prepared:

4-[3-(2',6'-dimethylphenyl)-1-propenyl]-2-ethylimidazole, M.p. of the hydrochloride 165°–172° C.

4-[4-(2'-chlorophenyl)-1-butenyl]-2-methylimidazole, M.p. of the hydrochloride 171°–174° C.

4-[4-(2',6'-dichlorophenyl)-1-butenyl]-2-methylimidazole, M.p. of the hydrochloride 197°–200° C.

4-[5-(2',6'-dimethylphenyl)-1-pentenyl]-2-methylimidazole $^{13}$C-NMR (hydrochloride): 12.745, 21.493, 29.939, 31.029, 34.904, 115.883, 116.912, 127.416, 129.929, 132.411, 135.983, 137.558, 140.827, 146.579

4-[6-(2',6'-dimethylphenyl)-1-hexenyl]-imidazole, M.p. of the hydrochloride 183°–189° C.

4-[6-(2',6'-dimethylphenyl)-1-hexenyl]-2-methylimidazole $^{13}$C-NMR (hydrochloride): 12.714, 21.463, 30.780, 30.787, 30.150, 34.420, 115.822, 116.549, 127.265, 129.838, 132.381, 136.165, 137.255, 140.918, 146.549

4-[2-(2',6'-dimethylphenyl)ethenyl]-3-benzylimidazole, M.p. of the hydrochloride 210°–218° C.

$^1$H-NMR (hydrochloride): 1.92 (s, 2H), 5.69 (s, 2H), 6.06 (d, 1H), 6.82 (s, 2H), 7.0–7.2 (m, 3H), 7.39 (s, 5H), 9.50 (d, 1H)

4-[3-(2',6'-dimethylphenyl)-1-propenyl]-3-benzylimidazole, M.p. of the hydrochloride 176°–180° C.

$^{13}$C-NMR: 19.34 (2C), 32.30, 49.31, 113.28, 115.58, 126.08, 127.21, 127.81, 128.11, 128.72, 131.84, 134.44, 135.05, 135.44, 135.71, 131.11

4-[2-(2',6'-dimethylphenyl)ethenyl]-3-ethylimidazole, M.p. of the hydrochloride 140°–148° C.

$^{13}$C-NMR (hydrochloride): 15.74, 19.92, 21.13, 43.59, 115.64, 116.91, 117.79, 128.78, 129.02, 129.08, 135.85, 136.62, 137.19

4-[3-(2',6'-dimethylphenyl)-1-propenyl]-3-ethylimidazole, M.p. of the hydrochloride 182°–186° C.

$^{13}$C-MNR (hydrochloride): 15.41, 20.04, 33.66, 43.38, 113.95, 116.61, 127.63, 129.20, 134.17, 135.26, 135.74, 137.71, 138.25

4-[5-(2',6'-dimethylphenyl)-1-pentenyl]-3-ethylimidazole, M.p. of the hydrochloride 165°–169° C.

$^{13}$C-MNR (hydrochloride): 15.56, 19.95, 29.30, 30.03, 34.39, 43.41, 114.34, 116.28, 126.57, 129.02, 134.41, 135.14, 136.74, 139.77, 140.74

4-[6-(2',6'-dimethylphenyl)-1-hexenyl]-5-methylimidazole

EXAMPLE 10

4-[2-(2',6'-dimethylphenyl)ethyl]-2-methylimidazole

The product is prepared by hydrogenation of 4-[2-(2',6'-dimethylphenyl)ethenyl]-2-methylimidazole in 80% ethanol using 9,8% palladium-on-carbon. The product is isolated as base into chloroform. The base is converted to the hydrochloride in isopropanol-ethylacetate. M.p. of the hydrochloride 198°–204° C.

$^1$H-NMR: 2.36 (s, 6H), 2.73 (s, 3H), 2.92 (m, 4H), 7.09 (s, 1H), 7.13 (s, 3H)

According to the same method for example the following compounds were prepared:

4-[5-(2',6'-dimethylphenyl)pentyl]-3-ethylimidazole, M.p. of the hydrochloride 149°–155° C.

$^{13}$C-MNR (hydrochloride): 15.44, 19.98, 24.127, 28.456, 29.94, 30.36, 30.52, 43.02, 117.31, 126.45, 128.99, 135.20, 136.47, 136.68, 140.10

4-[2-(2',6'-dimethylphenyl)ethyl]-3-ethylimidazole, M.p. of the hydrochloride 192°–200° C.

$^{13}$C-MNR (hydrochloride): 15.38, 19.89, 23.67, 28.73, 43.14, 117.91, 127.48, 129.32, 135.32, 135.98, 137.19, 137.56

4-[3-(2',6'-dimethylphenyl)propyl]-3-ethylimidazole, M.p. of the hydrochloride 195°–197° C.

$^{13}$C-MNR (hydrochloride): 15.41, 19.98, 24.31, 28.15, 29.85, 43.05, 117.43, 126.84, 129.11, 135.29, 136.26, 136.89, 139.01

EXAMPLE 11

4-(2',6'-dimethylbenzyl)-2-methylimidazole

The procedure of example 7 is repeated except that 4-[α-(2',6'-dimethylphenyl)hydroxymethyl]-2-methylimidazole is used.

M.p. of the base 162°–165° C.
M.p. of the hydrochloride 205°–208° C.

EXAMPLE 12

4-(2',6'-dimethylbenzyl)-3-methylimidazole and 4-(2',6'-dimethylbenzyl)-1-methylimidazole 3.0 g of 4-(2',6'-dimethylbenzyl)-imidazole, 40 ml of toluene, 3.0 g of methyliodide, 0.14 g of tetrabutylammoniumhydrogensulfate and 40 ml of 48% sodium hydroxide are mixed. The mixture is stirred vigorously for 2 hours at 70° C., after which the mixture is cooled and filtered. The toluene layer is separated from the mother liquid, after which it is washed with water and evaporated to dryness. The residue is a mixture of 4-(2',6'-dimethylbenzyl)-3-methylimidazole and 4-(2',6'-dimethylbenzyl)-1-methylimidazole. These two components are separated column chromatographically, eluting the column with a mixture of chloroform and methanol.

4-(2',6'-dimethylbenzyl)-3-methylimidazole:

$^1$H-NMR: 2.250 (s, 6H), 3.632 (s, 3H), 3.810 (s, 2H), 6.201 (s, 1H), 7.067 (s, 3H), 7.395 (s, 1H)

4-(2',6'-dimethylbenzyl)-1-methylimidazole:

¹H-NMR: 2.305 (s, 6H), 3.490 (s, 3H), 3.933 (s, 2H), 6.136 (s, 1H), 7.017 (s, 3H), 7.300 (s, 1H)

According to the same method, for example the following compounds were prepared:

4-[2-(2',6'-dimethylbenzyl)ethyl]-1-methylimidazole

¹³C-MNR (hydrochloride): 19.859, 24.914, 29.516, 36.236, 120.669, 127.356, 129.263, 135.499, 135.988, 137.134, 137.588

4-[2-(2',6'-dimethylphenyl)ethyl]-3-methylimidazole

¹³C-MNR (hydrochloride): 19.828, 23.219, 28.062, 33.754, 117.124, 127.083, 128.900, 128.900, 135.529, 135.681, 136.438

EXAMPLE 13

4-(2',6'-dimethylbenzyl)-3-tert.butylimidazole 4.44 g of 2,6-dimethylphenylacetaldehyde, 4.39 g of tert.butylamine, 100 ml of methanol and 5.86 g of tosylmethyl isocyanide are mixed. The mixture is stirred in room temperature for 1 hour after which it is refluxed for 3 hours. The mixture is evaporated to dryness, suspended in ether and filtered. The filtrate is dissolved in chloroform and washed with 2M-hydrochloric acid. The chloroform is evaporated to dryness and the residue is crystallized from ethyl acetate. The hydrochloride obtained (3 g) can be recrystallized from isopropanol. 2 g of product are obtained and it melts at 235°–237° C.

¹H-NMR (hydrochloride): 1.85 (s, 9H), 2.20 (s, 6H), 4.05 (s, 2H), 6.70 (s, 1H), 7.05 (s, 3H), 9.15 (s, 1H).

According to the same method, for example the following compounds were prepared:

4-(2',6'-dimethylbenzyl)-3-ethylimidazole, M.p. of the hydrochloride 221°–224° C.

4-(2',6'-dimethylbenzyl)-3-methylimidazole, M.p. of the hydrochloride 208°–214° C.

EXAMPLE 14

4-(2',6'-dimethylbenzyl)-1-(2'-chlorobenzyl)-imidazole 4-(2',6'-dimethylbenzyl)-3-(2'-chlorobenzyl)-imidazole 3.7 g of 4(5)-(2',6'-dimethylbenzyl)imidazole, 3.2 g of 2-chlorobenzylchloride, 0.2 g of tetrabutylammoniumhydrogensulfate, 5,8 g of 48% NaOH and 40 ml of toluene were mixed. The mixture was then stirred vigorously at 70° C. as long as the starting compound, 4(5)-(2',6'-dimethylbenzyl)imidazole could be detected by using thin layer chromatogrophic methods. The reaction mixture was cooled and filtered. The toluene layer was separated and extracted (3×20 ml of 1N HCl solution). The separated oil was extracted to methylene chloride which then was washed with 5% NaHCO₃-solution and water, and finally evaporated to dryness.

The residue is a mixture of the isomeric products. The components were separated through fractional recrystallization from ethylacetate. The hydrochlorides of the products were prepared in ethylacetate adding dry HCl-ethylacetate.

4-(2',6'-dimethylbenzyl)-1-(2'-chlorobenzyl)-imidazole. M.p. of the hydrochloride 231°–234° C.

¹H-NMR (HCl-salt): 2.029 (s, 6H), 3.716 (s, 2H), 5.771 (s, 2H), 6.374 (s, 1H), 7.041 (m, 3H), 7.290–7.412 (m, 4H), 9.670 (s, 1H), 15.61 (broad band, 1H)

4-(2',6'-dimethylbenzyl)-3-(2'-chlorobenzyl)-imidazole. M.p. of the hydrochloride 216°–220° C.

¹H-NMR (HCl): 2.231 (s, 6H), 4.155 (s, 2H), 5.493 (s, 2H), 6.295 (s, 1H), 7.068 (m, 3H), 7.068–7.52 (m, 5H), 9.678 (s, 1H)

According to the same method, for example the following compounds were prepared:

4-[2-(2',6'-dimethylbenzyl)ethyl]-1-(4'-methylbenzyl)-imidazole. M.p. of the hydrochloride 216°–219° C.

¹³C-NMR (HCl-salt): 19.889, 21.160, 24.006, 28.547, 52.734, 116.488, 126.206, 128.173, 128.627, 129.899, 130.413, 134.682, 134.773, 136.195, 136.347, 139.162

4-[2-(2',6'-dimethylphenyl)ethyl]-3-(4'-methylbenzyl)-imidazole, M.p. of the hydrochloride 180°–183° C.

¹³C-NMR (HCl-salt): 19.647, 21.100, 23.007, 27.941, 50.434, 117.033, 126.781, 127.477, 128.536, 126.778, 130.050, 134.137, 135.106, 135.923, 135.983, 139.162

4-(2',3'-dimethylbenzyl)-1-(4'-methylbenzyl)-imidazole

¹H-NMR (HCl-salt): 2.149 (s, 3H), 2.266 (s, 3H), 2.332 (s, 3H), 4.001 (s, 2H), 5.057 (s, 2H), 6.46 (s, 1H), 7.037–7.259 (m, 8H), 8.20 (s, 1H)

4-(2',3'-dimethylbenzyl)-3-(4'-methylbenzyl)-imidazole. M.p. of the hydrochloride 216°–219° C.

4-(2',6'-dimethylbenzyl)-1-(3'-methylbenzyl)-imidazole, M.p. of the hydrochloride 210°–212° C.

4-(2',6'-dimethylbenzyl)-3-(4'-methylbenzyl)-imidazole

¹H-NMR (HCl-salt): 1.995 (s, 6H), 2.304 (s, 3H), 3.685 (s, 2H), 5.643 (s, 2H), 6.382 (s, 1H), ~6.9–7.3 (m, 8H), 9.889 (s, 1H)

4-[2-(2',6'-dimethylphenyl)ethyl]-1-(2'-methylbenzyl)-imidazole. M.p. of the hydrochloride 215°–217° C.

¹H-NMR (HCl): 2.257 (s, 6H), 2.306 (s, 3H), 2.956 (board m, 4H), 5.492 (s, 2H), 6.482 (s, 1H), 6.951 (s, 3H), 7.250 (m, 5H), 9.724 (s, 1H)

4-[2-(2',6'-dimethylphenyl)ethyl]-1-(2',6'-dichlorobenzyl)-imidazole. M.p. of the base 140°–142° C.

¹H-NMR: 2.287 (s, 6H), 2.800 (m, 4H), 5.325 (s, 2H), 6.680 (s, 1H), 6.956 (s, 3H), 7.322 (m, 3H), 7.582 (s, 1H)

4-(2',3'-dimethylbenzyl)-1-(2',6'-dichlorobenzyl)-imidazole. M.p. of the hydrochloride 238°–241° C.

¹H-NMR: 2.134 (s, 3H), 2.266 (s, 3H), 4.118 (s, 2H), 5.618 (s, 2H), 6.618 (s, 1H), 7.064 (s, 3H), 7.397 (s, 3H), 9.020 (s, 1H)

4-(2',3'-dimethylbenzyl)-3-(2',6'-dichlorobenzyl)-imidazole

¹H-NMR (HCl): 2.138 (s, 3H), 2.313 (s, 3H), 4.062 (s, 2H), 5.518 (s, 2H), 6.851 (s, 1H), ~7.1 (m, 3H), 7.461 (s, 3H), 8.480 (s, 1H)

4-[2-(2',6'-dimethylphenyl)ethyl]-1-benzyl-imidazole. M.p. 202°–207° C.

¹H-NMR (hydrochloride): 2.14 (s, 6H), 2.5–3.1 (m, 4H), 4.91 (s, 1H), 5.32 (s, 2H), 6.97 (s, 3H), 7.1–7.5 (m, 6H), 8.99 (d, 1H)

4-[α-(2',6'-dimethylphenyl)hydroxymethyl]-3-(2'-chlorobenzyl)-imidazole. M.p. of the hydrochloride 139°–142° C.

¹H-NMR: 2.059 (s, 3H), 2.213 (s, 3H), 5.426 (s, 2H), 6.192 (s, 1H), 6.484 (s, 1H), 7.024–7.474 (m, 7H), 9.354 (s, 1H)

4-[α-(2',6'-dimethylphenyl)hydroxymethyl]-3-(3'-chlorobenzyl)-imidazole. M.p. of the hydrochloride 202°–205° C.

¹H-NMR (HCl): 2.249 (s, 6H), 2.309 (s, 3H), 5.240 (s, 2H), 6.324 (s, 1H), 6.499 (s, 1H), 7.003–7.173 (m, 7H), 9.155 (s, 1H)

We claim:

1. A substituted imidazole of the formula:

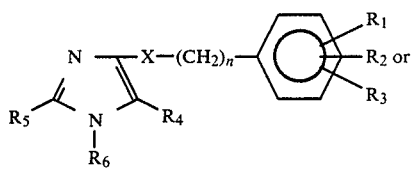

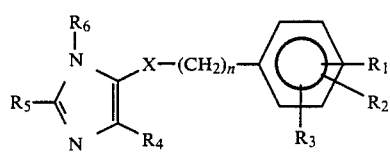

wherein each of $R_1$, $R_2$ and $R_3$, which can be the same or different, is hydrogen, chloro, bromo, fluoro, methyl, ethyl, methoxy, amino, hydroxy or nitro and at least one of $R_1$, $R_2$ and $R_3$ is other than hydrogen; $R_4$ is hydrogen or an alkyl radical of 1 to 7 carbon atoms; $R_5$ is hydrogen or a straight or branched alkyl group of 1 to 5 carbon atoms or a phenyl group; $R_6$ is hydrogen or an alkyl group of 1 to 7 carbon atoms or benzyl which is unsubstituted or substituted by chloro, bromo, fluoro, methyl, ethyl, methoxy, amino, hydroxy or nitro; X is —$CH_2$—, —CHOH— or —CH=CH—; and n is 0–4, provided that $R_5$ and $R_6$ are simultaneously hydrogen only when n is 4 and X is —CH=CH— and that when n is 2, X is CHOH, $R_1$, $R_2$, $R_4$ and $R_5$ are all hydrogen, and $R_6$ is methyl, then $R_3$ is a substituent other than 2-amino; and its nontoxic, pharmaceutically acceptable acid addition salts.

2. A pharmaceutical composition useful for reducing or preventing thrombosis comprising an effective amount of a compound selected from the class consisting of a substituted imidazole of the formula:

(I)

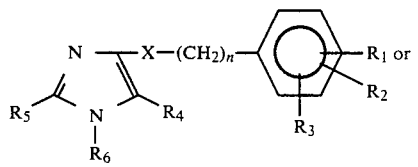

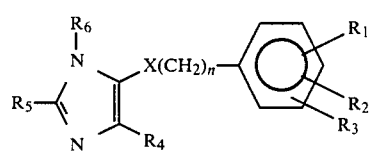

wherein each of $R_1$, $R_2$ and $R_3$, which can be the same or different, is hydrogen, chloro, bromo, fluoro, methyl, ethyl, methoxy, amino, hydroxy or nitro and at least one of $R_1$, $R_2$ and $R_3$ is other than hydrogen; $R_4$ is hydrogen or an alkyl radical of 1 to 7 carbon atoms; $R_5$ is hydrogen or a straight or branched alkyl group of 1 to 5 carbon atoms or a phenyl group; $R_6$ is hydrogen or an alkyl group of 1 to 7 carbon atoms or benzyl which is unsubstituted or substituted by chloro, bromo, fluoro, methyl, ethyl, methoxy, amino, hydroxy or nitro; X is —$CH_2$—, —CHOH— or —CH=CH—; n is 0–4, provided that $R_5$ and $R_6$ are simultaneously hydrogen only when n is 4 and X is —CH=CH—; and its non-toxic pharmaceutically acceptable acid addition salts, and a compatible pharmaceutically acceptable carrier therefor.

3. A method of reducing and preventing thrombosis which comprises administering to a patient subject thereto an effective amount of a compound selected from the glass consisting of a substituted imidazole of the formula:

(I)

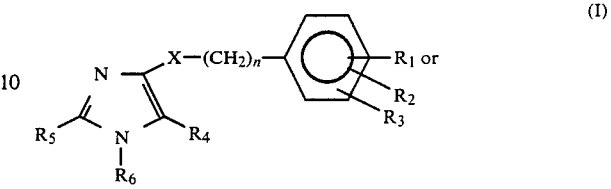

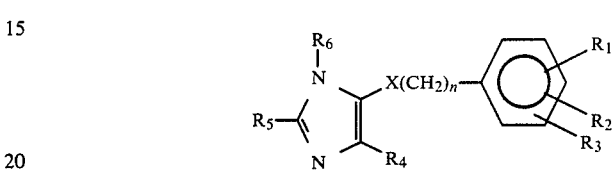

wherein each of $R_1$, $R_2$ and $R_3$, which can be the same or different, is hydrogen, chloro, bromo, fluoro, methyl, ethyl, methoxy, amino, hydroxy or nitro and at least one of $R_1$, $R_2$ and $R_3$ is other than hydrogen; $R_4$ is hydrogen or an alkyl radical of 1 to 7 carbon atoms; $R_5$ is hydrogen or a straight or branched alkyl group of 1 to 5 carbon atoms or a phenyl group, $R_6$ is hydrogen or an alkyl group of 1 to 7 carbon atoms or benzyl which is unsubstituted or substituted by chloro, bromo, fluoro, methyl, ethyl, methoxy, amino, hydroxy, or nitro; X is —$CH_2$—, —CHOH— or CH=CH—; and n is 0–4, provided that $R_5$ and $R_6$ are simultaneously hydrogen only when n is 4 and X is —CH=CH—; and its non-toxic pharmaceutically acceptable acid addition salts.

4. A method of reducing or preventing hypertension which comprises administering to a patient subject thereto an effective amount of a compound selected from the class consisting of a substituted imidazole of the formula:

(I)

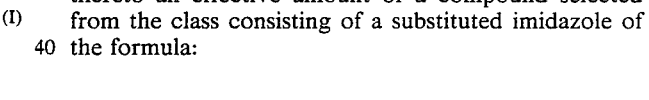

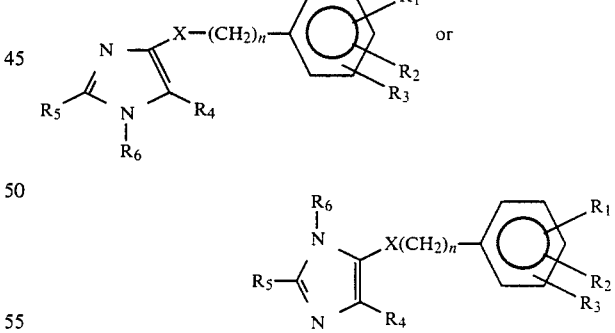

wherein each of $R_1$, $R_2$ and $R_3$, which can be the same or different, is hydrogen, chloro, bromo, fluoro, methyl, ethyl, methoxy, amino, hydroxy or nitro and at least one of $R_1$, $R_2$ and $R_3$ is other than hydrogen; $R_4$ is hydrogen or an alkyl radical of 1 to 7 carbon atoms; $R_5$ is hydrogen or a straight or branched alkyl group of 1 to 5 carbon atoms or a phenyl group; $R_6$ is hydrogen or an alkyl group of 1 to 7 carbon atoms or benzyl which is unsubstituted or substituted by chloro, bromo, fluoro, methyl, ethyl, methoxy, amino, hydroxy, or nitro; X is —$CH_2$— and n is 0 or 1; and its non-toxic pharmaceutically acceptable acid addition salts.

5. A method of preventing the growth of, or killing, microbes which comprises applying to a locus in which such microbes are, or may be, present an effective amount of a compound selected from the class consisting of a substituted imidazole of the formula:

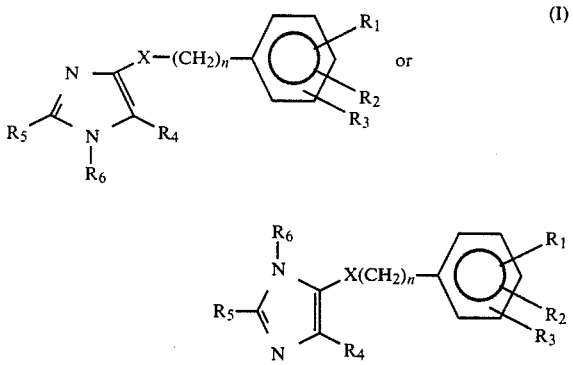

wherein each of $R_1$, $R_2$ and $R_3$, which can be the same or different, is hydrogen, chloro, bromo, fluoro, methyl, ethyl, methoxy, amino, hydroxy or nitro and at least one of $R_1$, $R_2$ and $R_3$ is other than hydrogen; $R_4$ is hydrogen or an alkyl radical of 1 to 7 carbon atoms; $R_5$ is hydrogen or a straight or branched alkyl group of 1 to 5 carbon atoms or a phenyl group; $R_6$ is hydrogen or an alkyl group of 1 to 7 carbon atoms or benzyl which is unsubstituted or substituted by chloro, bromo, fluoro, methyl, ethyl, methoxy, amino, hydroxy, or nitro; X is —CH=CH—; and n is 1–4, provided that $R_5$ and $R_6$ are simultaneously hydrogen only when n is 4; and its non-toxic pharmaceutically acceptable acid addition salts."

6. A compound according to claim 1 wherein each $R_1$, $R_2$ and $R_3$, which can be the same or different, is hydrogen, chloro, methyl, ethyl or methoxy, at least one being other than hydrogen.

7. A compound according to claim 1 wherein $R_4$ is hydrogen or methyl.

8. A compound according to claim 1 wherein $R_4$ is hydrogen.

9. 4-(2',6'-dimethylbenzyl)-2-methylimidazole and its non-toxic pharmaceutically acceptable acid addition salts.

10. 4-(2',6'-dimethylbenzyl)-2-ethylimidazole and its non-toxic pharmaceutically acceptable acid addition salts.

11. 4-(2',6'-dimethylbenzyl)-2-n-butylimidazole and its non-toxic pharmaceutically acceptable acid addition salts.

12. 4-[3-(2',6'-dimethylphenyl)-1-hydroxypropyl]-2-ethylimidazole and its non-toxic pharmaceutically acceptable acid addition salts.

13. 4-[2-(2',6'-dimethylphenyl)-1-hydroxyethyl]-3-benzylimidazole and its non-toxic pharmaceutically acceptable acid addition salts.

14. 4-[3-(2',6'-dimethylphenyl)-1-hydroxypropyl]-3-benzylimidazole and its non-toxic pharmaceutically acceptable acid addition salts.

15. 4-[5-(2',6'-dimethylphenyl)-1-hydroxypentyl]-3-ethylimidazole and its non-toxic pharmaceutically acceptable acid addition salts.

16. 4-[3-(2',6'-dimethylphenyl)-1-hydroxypropyl]-3-ethylimidazole and its non-toxic pharmaceutically acceptable acid addition salts.

17. 4-[5-(2',6'-dimethylphenyl)pentyl]-3-ethylimidazole and its non-toxic pharmaceutically acceptable acid addition salts.

18. 4-[3-(2',6'-dimethylphenyl)propyl]-3-ethylimidazole and its non-toxic pharmaceutically acceptable acid addition salts.

19. 4-[2-(2',6'-dimethylphenyl)ethyl]-2-methylimidazole and its non-toxic pharmaceutically acceptable acid addition salts.

20. 4-(2',6'-dimethylbenzyl)-3-methylimidazole and its non-toxic pharmaceutically acceptable acid addition salts.

21. 4-(2',6'-dimethylbenzyl)-3-ethylimidazole and its non-toxic pharmaceutically acceptable acid addition salts.

22. 4-[3-(2',6'-dimethylphenyl)-1-propenyl]-2-ethylimidazole and its non-toxic pharmaceutically acceptable acid addition salts.

23. 4-[4-(2',6'-dichlorophenyl)-1-butenyl]-2-methylimidazole and its non-toxic pharmaceutically acceptable acid addition salts.

24. 4-[5-(2',6'-dimethylphenyl)-1-pentenyl]-2-methylimidazole and its non-toxic pharmaceutically acceptable acid addition salts.

25. 4-[6-(2',6'-dimethylphenyl)-1-hexenyl]-5-methylimidazole and its non-toxic pharmaceutically acceptable acid addition salts.

26. 4-[6-(2',6'-dimethylphenyl)-1-hexenyl]-imidazole and its non-toxic pharmaceutically acceptable acid addition salts.

27. 4-[6-(2'-chlorophenyl)-1-hexenyl]-imidazole and its non-toxic pharmaceutically acceptable acid addition salts.

28. 4-[6-(2',6'-dichlorophenyl)-1-hexenyl]-5-methylimidazole and its non-toxic pharmaceutically acceptable acid addition salts.

29. 4-[6-(2'-chlorophenyl)-1-hexenyl]-5-methylimidazole and its non-toxic pharmaceutically acceptable acid addition salts.

* * * * *